United States Patent [19]

Sampson et al.

[11] 4,286,584
[45] Sep. 1, 1981

[54] SEPTUM LOCATING APPARATUS

[75] Inventors: Edward J. Sampson, Concord; Frank R. Prosl, Duxbury, both of Mass.

[73] Assignee: Infusaid Corporation, Sharon, Mass.

[21] Appl. No.: 85,125

[22] Filed: Oct. 15, 1979

Related U.S. Application Data

[62] Division of Ser. No. 916,129, Jun. 16, 1978, Pat. No. 4,222,374.

[51] Int. Cl.³ .............................................. A61B 19/00
[52] U.S. Cl. ........................................... 128/1 R; 3/1
[58] Field of Search ............... 128/1 R, 1.3, 130, 213, 128/260, 419 PG; 3/1, 1.5; 324/259–262, 214, 215

[56] References Cited

U.S. PATENT DOCUMENTS

| 3,293,544 | 12/1966 | Seng | 324/214 |
| 3,443,214 | 5/1969 | Meservey | 324/214 |
| 3,765,414 | 10/1973 | Arlen | 128/260 |

OTHER PUBLICATIONS

Morey, "RCA Technical Note No. 675", Jun. 1966, 1 page.
Newbewer, "IEEE Transactions on Magnetics", vol. 9, No. 3, Sep. 1973, pp. 447–450.

Primary Examiner—William E. Kamm
Attorney, Agent, or Firm—Cesari and McKenna

[57] ABSTRACT

Apparatus for locating the septum through which an implanted prosthetic device is refilled with infusate includes means mounted in the device in juxtaposition with the septum for producing an energy pattern that extends outside the body. The pattern is shaped so as to indicate the location under the skin of the septum of the implanted device. The apparatus also includes a small portable detector which is responsive to the radiation pattern emanating from the body. The detector is arranged so that when manipulated over the patient's body at the approximate site of the implanted device, it designates the location of the septum.

2 Claims, 11 Drawing Figures

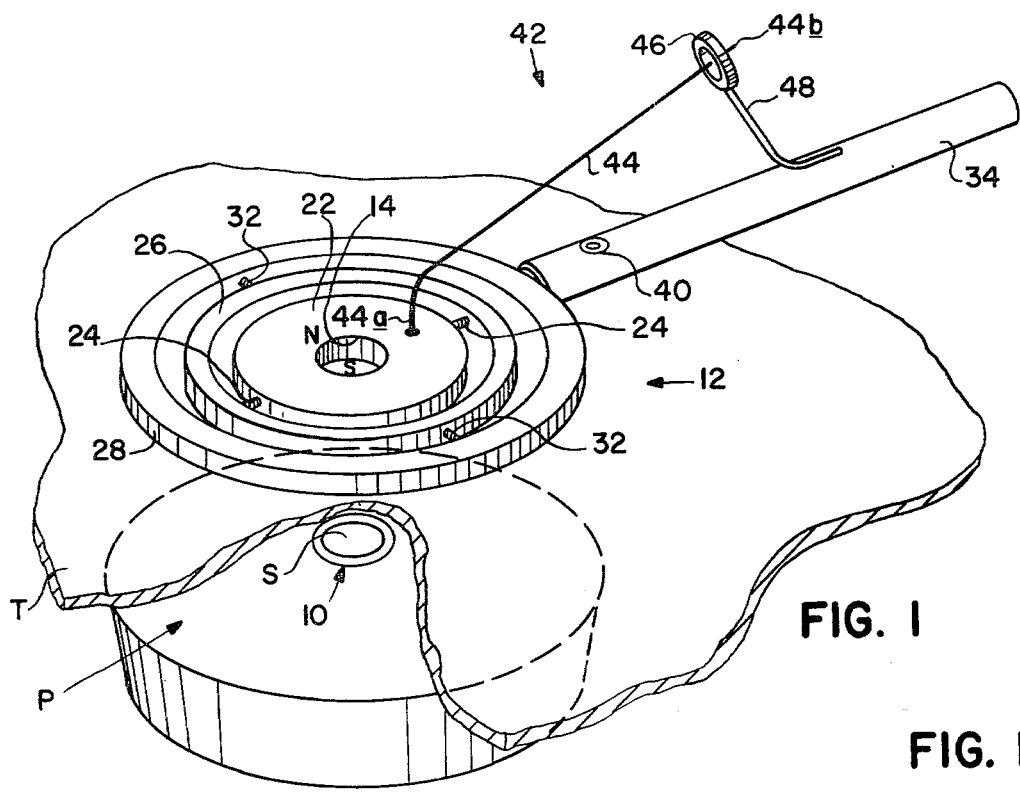
FIG. 1
FIG. 1A
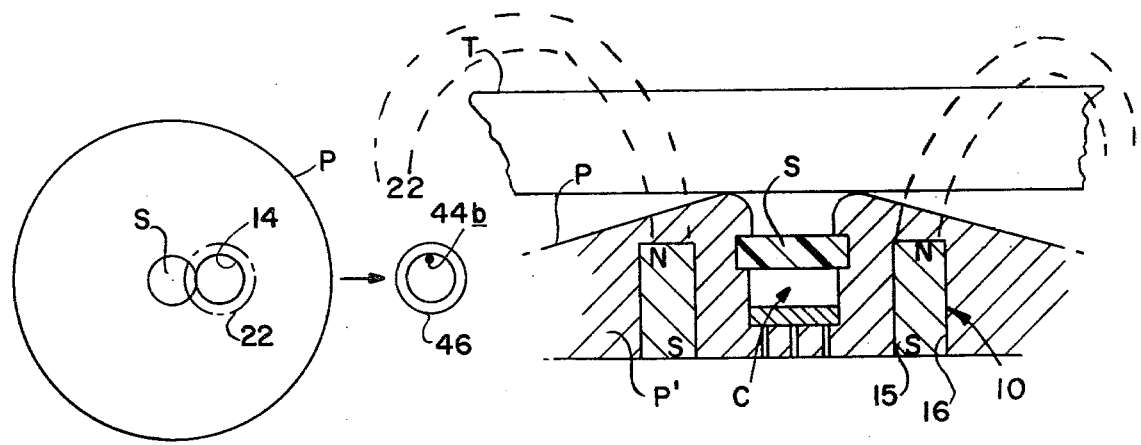
FIG. 2A
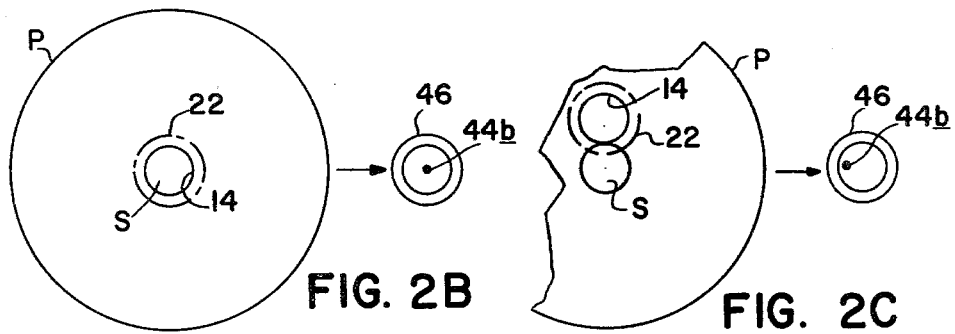
FIG. 2B
FIG. 2C

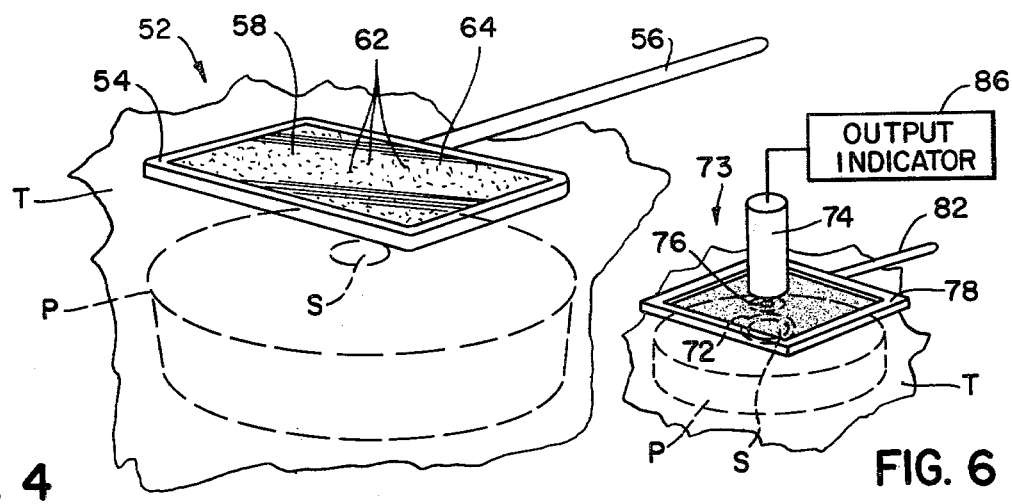
FIG. 4
FIG. 6
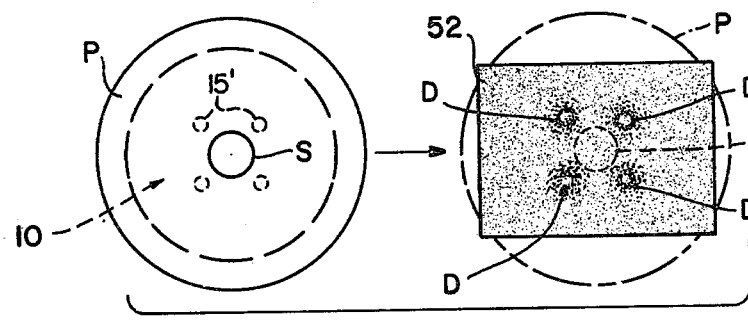
FIG. 5A
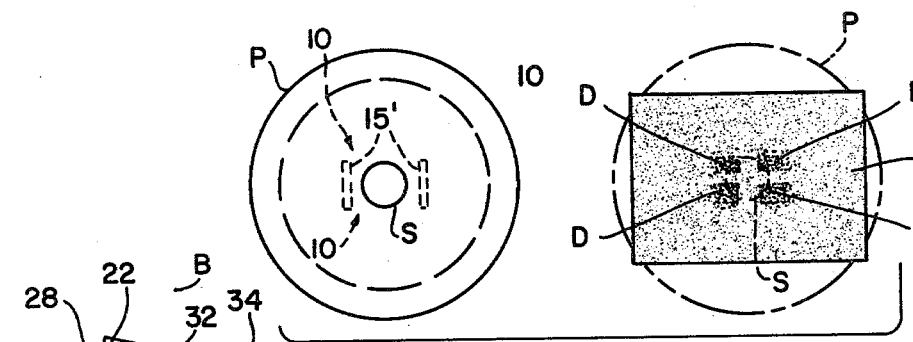
FIG. 5B
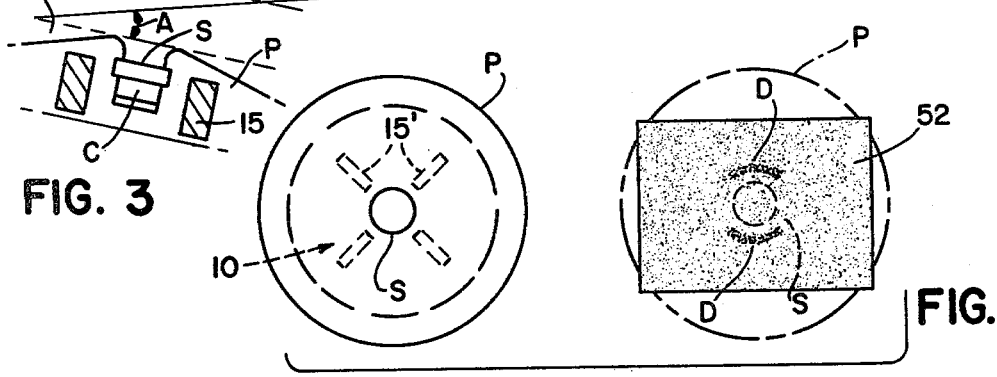
FIG. 3
FIG. 5C

SEPTUM LOCATING APPARATUS

This is a division of application Ser. No. 916,129 filed June 16, 1978, now U.S. Pat. No. 4,222,374.

This invention relates to apparatus for accurately locating the septum through which the fluid reservoir of an implanted prosthetic device may be refilled subcutaneously.

BACKGROUND OF THE INVENTION

Relatively recently, implantable prosthetic devices in the nature of infusate pumps have been developed for dispensing infusates such as insulin at a very low flow rate to a selected location in the human body over the long term. Eventually the fluid reservoir in such a device empties so that, if the device is to continue performing its function, its reservoir must be refilled with a fresh supply of infusate. To avoid having to operate on a patient to remove the implanted device each time it is necessary to refill it, the device is designed with a penetrable self-sealing septum in a wall of the device which normally seals a passage leading to the device's reservoir.

With the pump or other device implanted in the patient's body so that the septum underlies the skin, its reservoir can be refilled, as needed, simply by injecting a fresh supply of infusate by means of a hypodermic needle through the patient's skin, through the septum and into the infusate reservoir or chamber inside the device. In some cases, the act of refilling the device also recharges its power supply so that the unit can operate uninterruptedly for a prolonged period. Implantable pumps of this general type are disclosed, for example, in U.S. Pat. No. 3,731,681 and 3,951,147.

Other rechargeable, battery-operated implantable devices such as pumps and pacemakers have septums through which needle-like electrical terminals are injected to make contact with terminals inside the devices leading to the battery.

In some cases, it has proven difficult to locate the septum of the implanted device in order to inject a needle into it to refill or recharge the device. One reason for this difficulty is that the physical movements of the patient after the device is implanted sometimes causes the device to shift its position within the body so that its septum is no longer at its original location. Thus a physician cannot rely on a datum such as a tatoo marked on the patient's body to pinpoint the septum after the device is implanted.

It should be mentioned at this point also that the implanted device may not only shift laterally relative to its original position, but also it may cock or tilt so that its septum is skewed relative to the overlying surface of the patient's body. Thus, even if the device's septum underlies the original datum, when the hypodermic is inserted through the patient's skin, it may pierce the septum at a considerable angle so that the needle does not seat properly at the charging station of the device. Also, in a worst case situation, the needle point may strike a hard surface inside the implanted device and be broken.

The septum locating problem is particularly acute in the case of very heavy or obese people because the implanted device underlies several layers of fatty tissue and is more apt to shift its position within the body.

Until now, there has been no easy way to precisely pinpoint the location of the septum of such an implanted device except for repeated injections on a trial and error basis. This procedure is not only painful to the patient, but also it opens the possibility of the infusing hypodermic needle missing the septum entirely unbeknownst to the physician. In that event, a relatively large quantity of infusate could be injected locally into the patient all at once with possibly harmful results. Also as alluded to previously, unless the needle is aimed properly, it could strike a hard surface of the device and break within the patient's body with equally distressing results.

SUMMARY OF THE INVENTION

Accordingly, it is an object of the present invention to provide apparatus for precisely locating the refilling or recharging septum of a device implanted within a body.

Another object of the invention is to provide septum locating apparatus which is able to indicate not only the lateral position of the implanted septum but also its angle of tilt within the body.

Yet another object of the invention is to provide septum locating apparatus which is self-contained and requires no external power supply.

Another object is to provide such apparatus that locates the septum of an implanted device even if the device shifts its position within the body.

A further object of the invention is to provide septum locating apparatus which is small and easy to use.

Yet another object of the invention is to provide such apparatus which is relatively inexpensive to make and requires minimum maintenance.

Other objects will in part be obvious and will in part appear hereinafter.

The invention accordingly comprises the features of construction, combination of elements and arrangement of parts which will be exemplified in the following detailed description, and the scope of the invention will be indicated in the claims.

Briefly, the present septum locating apparatus comprises means mounted in the implanted device for producing an energy pattern that emanates from the patient's body. The pattern is shaped so as to "target" the device's septum that underlies the patient's skin. In one embodiment of the invention, the energy pattern producing means is one or more permanent magnets which are shaped and/or arranged relative to the septum so as to generate a magnetic field pattern external to the patient's body which indicates the septum's location.

In a further embodiment, the energy pattern producing means comprises one or more sources of corpuscular radiation mounted in the implanted device in juxtaposition with its septum so that the radiation pattern emanating from the patient's body provides an indication of the septum location. Of course, other such external field or radiation producing sources can be incorporated into the implanted device and arranged relative to its septum so as to indicate septum location.

The septum locating apparatus also includes a small hand-held detector that is responsive to the energy pattern produced by the septum-designating source incorporated into the implanted device. When the detector is moved along the patient's body over or adjacent the general vicinity of the implanted device, the detector responds to the energy pattern by producing a visible indication of the location of the septum relative to the detector. Thus following these indications, the physician manipulating the detector can steer the detector until a reticle on the detector directly overlies the implanted septum. Then using the reticle as an aiming point, the physician can mark the patient's skin and be assured that the implanted septum is located directly underneath that mark.

The precise form of the detector depends of course on the nature of the energy producing source. In the case of a magnetic source, the detector would also include a ferromagnetic component or part which may be a magnet or nonmagnet that responds to the field generated by the magnetic source so as to align itself depending upon the location of the detector relative to the implanted magnetic source. When the detector's reticle is located precisely above the septum, the detector component has a characteristic orientation or disposition indicating that fact. On the other hand, if the energy producing source is nuclear in nature, the detector includes radiation sensing means whose output is maximized when the detector reticle is directly above the septum.

Using the present apparatus, then, the physician can precisely locate the septum of an implanted device even though the device has shifted relative to its original position when implanted. Further, should the device tilt in the body after implantation so that its septum is skewed relative to the adjacent skin layers, some locating apparatus embodiments also indicate that fact. Resultantly, the physician can insert the infusate injection syringe into the patient's body at an angle so that its needle always penetrates the device's septum orthogonally. Resultantly there is little likelihood of the needle not seating properly in the device's charging station or striking hard surfaces that may cause damage to the needle.

Also in the event that the same implanted device has more than one septum, separate energy-emitting sources can be associated with the septums, which sources produce different characteristic energy patterns. In this way, the physician can discriminate between the different septums.

With all of the aforesaid advantages, the present apparatus is still relatively simple, requires no external power supply and is relatively easy to make and to use. Therefore, it should find wide application whenever septum-containing implanted prosthetic devices have to be refilled or serviced by injection through those septums after implantation.

BRIEF DESCRIPTION OF THE DRAWINGS

For a fuller understanding of the nature and objects of the invention, reference should be had to the following detailed description taken in connection with the accompanying drawings in which:

FIG. 1 is a perspective view with parts cut away showing the subject septum locating apparatus in conjunction with an implanted infusate pump;

FIG. 1A is a fragmentary sectional view showing a portion of the FIG. 1 apparatus and implanted pump in greater detail;

FIGS. 2A to 2C are diagrammatic view illustrating the operation of the FIG. 1 apparatus;

FIG. 3 is a diagrammatic view of the FIG. 1 apparatus illustrating its mode of operation;

FIG. 4 is a perspective view showing a modified embodiment of the apparatus;

FIGS. 5A to 5C are diagrammatic views illustrating the operation of the FIG. 4 apparatus embodiment, and FIG. 6 illustrates still another apparatus embodiment.

DESCRIPTION OF THE PREFERRED EMBODIMENTS

Turning now to FIG. 1 of the drawings, the subject septum locating apparatus is designed to facilitate locating the septum S of an implantable prosthetic device such as an infusate pump P implanted in a patient's body such that the septum S is located directly under the patient's skin layers T. The locating apparatus includes an energy pattern source indicated generally at 10 which is mounted in the implanted pump P. Source 10 is juxtaposed relative to septum S so that the source's radiation pattern emanates from the patient's body and is shaped or configured so that it indicates the location of the septum.

The locating apparatus also includes an extracorporeal hand-held detector shown generally at 12 having a reticle 14. The detector has one or more components which are responsive to the energy pattern emanating from source 10 so as to indicate the lateral deviation of the reticle from the center line of the septum. By manipulating the detector following these indications, the physician can easily center the reticle directly above the septum and mark the target point on the patient's body. Then he can inject the infusate injection apparatus through that mark with assurance that it will penetrate the underlying septum S and be positioned properly in the charging station C of pump P (FIG. 1A).

In the apparatus embodiment illustrated in FIGS. 1 and 1A, the source 10 comprises an annular permanent magnet 15 mounted in a recess 16 in the underside of the pump wall P'. Magnet 15 is preferably a sintered rare earth magnet that is polarized in the axial direction as indicated in FIG. 1A. Thus it produces a strong toroidal magnetic field shown in dotted lines at M in that figure whose flux lines extend an appreciable distance out from the surface of the patient's body.

Also as seen in FIG. 1, the detector 12 comprises a second similar annular rare earth magnet 22, the center opening of which constitutes the detector reticle 14. Preferably, the magnet is axially polarized in the same direction as magnet 15 when supported as shown in in FIG. 1. The magnet produces a toroidal field like field M (FIG. 1A) which extends appreciably below detector 12. The magnet 22 is connected by a pair of diametrically opposite pivots 24 to a ring 26 outboard of and concentric with the magnet. Ring 26 is, in turn, connected to an even larger concentric ring 28 by diametrically opposite pivots 32 which are disposed at right angles to pivots 24. These rings function as gimbals so that magnet 22 is free to pivot about mutually orthagonal axes relative to the outermost ring 28. A handle 34 aligned with pivots 24 is attached to the outermost ring 28 to facilitate holding the detector.

The rings 26 and 28 and the pivots 24 and 32 are all made of a non-ferromagnetic material such as brass, aluminum or plastic which are unaffected by the magnetic fields produced by magnets 15 and 22. Also, the pivots 24 and 32 are located so that the centers of mass of magnet 22 and ring 26 are located below their respective pivots so that in the absence of any magnetic field acting upon magnet 22, the magnet tends to position itself in a horizontal plane because of the gravitational forces acting upon it. Assuming then that the outer ring 28 is maintained substantially horizontal by the user, the magnet 22 will also lie in a horizontal plane parallel to ring 28. A bubble type level indicator 40 may be mounted in handle 34 to help the physician maintain ring 28 horizontal.

To enable the physician to determine immediately the amount and direction of the deviation of ring 22 from the plane of ring 28, an indicator shown generally at 42 is provided. Indicator 42 includes a long wand or pointer 44 one of whose ends 44a is secured to magnet 22 at a location radially inboard of handle 34. The pointer 44 is curved toward the handle so that its opposite end 44b lies more or less parallel to the handle. The pointer end 44b projects through a ring 46 that is connected by way of a bracket 48 to the top surface of handle 34.

The pointer 44 and ring 46 are arranged so that the pointer end 44b is centered in the ring 46 when the magnet 22 lies parallel to ring 28. That is, the ring center defines a target or bench mark for the pointer. However, should magnet 22, as shown in FIG. 1, tilt counterclockwise about pivots 32, that movement is indicated by the upward movement of pointer 44 in ring 46. On the other hand, a clockwise pivoting movement of magnet 22 results in a downward movement of the pointer within ring 46. Likewise, tilting movements of the magnet 22 to the left or right relative to handle 34 manifest themselves in movements of the pointer within ring 46 to the left or right respectively.

In order to locate septum S in the implanted pump P, the physician, using handle 34, positions the detector 12 a few inches above the general location of the implanted pump P. As soon as the detector's magnet 22 is positioned sufficiently close to magnet 15, their magnetic fields interact so as to cause magnet 22 to tilt on its gimbals in one direction or another from a horizontal plane. Assume, for example, that the detector 12 is being moved from right to left, in FIG. 1, so that magnet 22 approaches magnet 15 from the right. In this event, the left-hand edge of magnet 22 will encounter and be attracted by the right-hand edge of magnet 15 causing magnet 22 to tilt counter-clockwise on its gimbals. This movement causes pointer 44 to assume a position in the extreme upper portion of the ring 46 as shown in FIG. 2A.

As the detector continues to be moved leftward, more of magnet 22 will be disposed above magnet 15 so that the right-hand edge of magnet 15 will tend to attract portions of magnet 22 to the right of the gimbal pivots 32. This causes magnet 22 to tilt clockwise so as to lie more nearly in a horizontal plane. Since the magnetic fields produced by the two magnets are symmetric about their respective axes, when the magnet 22 is located directly above magnet 15, the magnetic forces acting on magnet 22 are equalized so that magnet 22 is disposed in a horizontal plane. In this position, the detector reticle 14 is located directly above septum S as shown in FIG. 2B and this fact is indicated by the pointer 44 being centered within the sighting ring 46.

As detector 12 is moved still further leftward, the attractive force of magnet 15 on magnet 22 will be stronger to the right of the gimbal pivot 32 so that the magnet 22 will tend to tilt clockwise resulting in a downward movement of pointer 44 in ring 46.

The same situation prevails with respect to movements of the detector 12 relative to the pump P transverse to the handle 34 axis. Thus as shown in FIG. 2C, if the detector reticle 14 is positioned "above" septum S as shown in that figure, the force on magnet 22 will be stronger to the left of its pivots 24 so that the magnet will tilt counterclockwise resulting in pointer 44 being moved toward the left hand extreme in the sighting ring 46 as shown in FIG. 2C.

It will be appreciated from the foregoing, then, that the physician, by watching the pointer 44 position within the ring 46, can manipulate the detector 12 above septum S until the movement of the magnet 22 reaches a null position; in other words, so that movements of the detector laterally in opposite directions from that null position cause opposite pivotal movements of magnet 22 on its gimbals. At the null position, assuming that the implanted magnet 15 is more or less horizontal, the magnet 22 will lie parallel to ring 28 and the pointer of 44 will be centered in the sighting ring 46. At this point, the physician can insert a marker through the reticle 14 or under the detector and mark the point on the patient's skin T directly below the reticle 14 as shown at X in FIG. 2B. The physician can then inject the infusion apparatus through that mark directly through the underlying septum S and into the pump's charging station C (FIG. 1A).

In certain cases, the pump P may move in the patient's body so that its septum S and therefore its magnet 15 become skewed relative to the overlying skin layers T. The present apparatus is able to detect this shift in movement and provide an indication to the physician so that he will insert the needle of the infusion apparatus through the patient's skin at an angle so that the needle will be perpendicular to the implanted septum S as it penetrates the septum.

More particularly and referring to FIG. 3, when the implanted magnet 15 is oriented at an angle A relative to the horizontal as shown in that figure, if the detector 12 is scanned over the general site of the implanted device as described above, the normally horizontal magnet 22 will be tilted in one direction or another on its gimbals. By observing the direction of tilt, the physician can manipulate the detector to find a null position of the magnet from which movements of the detector in opposite directions cause the magnet 22 to tilt in opposite directions, all as described above. At that point, the physician knows that the detector is targeted on the septum.

However, because of the symmetry of the magnetic fields produced by the two magnets 15 and 22, the magnet 22 tends to assume an orientation that makes it coaxial and parallel with magnet 15 even though the latter magnet is skewed relative to the horizontal. Accordingly, magnet 22 assumes an orientation in its null position that makes it parallel and coaxial to magnet 15 as illustrated in FIG. 3. Since the physician observes the magnet 22 tilted while in its null position, he immediately knows that the pump P has shifted within the body after its implantation such that its magnet 15 and septum S now lie at the same angle A relative to skin layers T as magnet 22 lies relative to the horizontal handle 34. Accordingly, the physician can determine the proper angle of entry into the body of the infusate injection needle simply by sighting through the reticle 14. Thus if the needle is inserted along the direction of arrow B in FIG. 3, the needle will be perpendicular to the septum S when it penetrates the septum and enters the pump's charging station C.

Turn now to FIG. 4 which shows a modified detector 52 for use in the subject septum locating apparatus. Detector 52 comprises a thin, hollow, wafer-like plastic capsule 54 having a handle 56. Capsule 54 is filled with a so-called ferrofluid 58 which comprises a multiplicity of tiny ferromagnetic particles 62 suspended in a liquid carrier 64. A suitable ferrofluid can be obtained, for example, from Ferrofluidics Corporation, Burlington, Mass.

When a ferrofluid is subjected to a magnetic field, the particles 62 move in the carrier 64 so as to concentrate themselves along the magnetic flux lines. Therefore, by observing the distribution of the particles, one can immediately discern the shape of the magnetic field. The shape and strength of the field, in turn, is determined by the shape or distribution of the magnets producing the field. Thus, a given magnetic source produces a characteristic magnetic field pattern. Consequently, when the ferrofluid detector 52 is placed directly above the magnetic source, its particles assume a characteristic pattern. When the detector 52 is moved laterally relative to the source, the particle pattern moves in the opposite direction within capsule 58. Thus, if the magnetic source is properly juxtaposed relative to the septum S in the implanted device, the particle pattern produced by detector 52 can be used to "target" or locate the septum.

FIGS. 5A to 5C illustrate three different arrangements of magnets 15' positioned in pump P around its septum S. To the right of each of those three figures are diagrammatic views showing the particle pattern produced when indicator 52 is positioned above the implanted pump P. Thus in FIG. 5A, the four small discoid magnets 15' bracketing septum S produce a pattern of particles 62 in detector 52 comprising four spots D arranged in a square. By observing the location and density of those spots, the physician is assured that the septum S of the implanted pump is located directly below and parallel to the center of the square defined by the four spots which thus constitutes the detector reticle 14.

The pump depicted in FIG. 5B has a pair of oppositely polarized bar magnets 15' located on opposite sides of septum S. This particular arrangement produces a distribution of particles 62 in detector 52 that forms a relatively transparent cross or X in the detector capsule. In other words, the particles tend to concentrate along the horizontal lines between the opposite magnetic poles. In addition, however, the bucking fields created along the diagonals between the magnets disperse the particles so as to form four triangular spots D defining the legs of the X. Thus the X effectively forms a detector reticle 14 in the form of cross-hairs that pinpoint the exact location of the underlying septum.

FIG. 5C shows a pump P having a radial array of magnets 15' distributed about the septum. This array of magnets produces a particle pattern composed of upper and lower arcs which bracket the location of the underlying septum.

Of course, a variety of other magnet shapes and/or distributions can be envisioned that would distribute the detector particles 62 in such a way as to pinpoint the septum S even though the septum is implanted in the body and completely hidden from view.

FIG. 6 depicts another septum locating apparatus in which the energy pattern-emitting source positioned in the pump around the septum comprises an annular deposit of weakly radioactive material 72. The detector shown generally at 73 in this embodiment comprises a radiation sensor 74 mounted behind an aperture 76 or reticle in a radiation screen in the form of a lead sheet 78 having a handle 82. The electrical output from the sensor is applied to an output indicator 86 such as a meter or scope. In this embodiment, the physician scans the detector 73 over the general vicinity of the implanted pump P. The lead sheet 78 shields the sensor 74 from the radiation particles emanating from the source material 72 which particles can be considered as traveling in straight lines over the short distances involved. Consequently, the sensor produces little or no output. However, when the aperture 76 is located directly above the radiation source 72, the radiation particles pass through aperture 76 into the sensor. The sensor thereupon produces an electrical output to the output indicator 86 that signals the physician that the detector aperture 76 is located directly above the source 72 and therefore directly above the septum S. He can then mark the spot on the patient's body that is directly under the aperture or reticle 76.

Of course, if the implanted device contains more than one septum different sources 10 therein may be arranged to produce different energy patterns. For example, one source 10 in that device might produce the pattern shown in FIG. 5A, while another source 10 produces the pattern shown in FIG. 5B or is a radiation source 72 (FIG. 6). This arrangement permits the doctor to identify and discriminate between different septums through which different fluids should be injected or which seal charging stations used for different purposes.

The septum locating apparatus embodiments described above are relatively simple and inexpensive to make and very easy to use. Furthermore, the first two require no external sources of power so that they are safe to use even in the potentially explosive environment of a hospital operating room. As noted above, the present apparatus enables the physician to precisely locate the septum of a prosthetic device implanted in the human body even though that device has shifted from its original position and even though it is located below layers of fatty tissue. Consequently, it should find wide application in hospitals and clinics where such implanted devices are serviced periodically.

It will thus be seen that the objects set forth above among those made apparent from the preceding description are efficiently attained and since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described.

We claim:
1. Apparatus for locating a septum in a prosthetic device implanted in a body comprising:
 A. at least one permanent magnet mounted in the device in selected juxtaposition with the septum for emitting a magnetic field that extends exteriorly of the body and whose pattern defines the location of the septum, and
 B. a passive nonelectric detector manipulable exteriorly of the body, said detector including
   1. a container, and
   2. a multiplicity of ferromagnetic particles in the container, the particles assuming a characteristic disposition in the container that corresponds to the magnetic field pattern produced by the said at least one implanted magnet thereby visually designating the precise location of the patient's body surface under which the septum is implanted.
2. The apparatus defined in claim 1 wherein the ferromagnetic particles comprise a ferrofluid.

* * * * *